United States Patent [19]

Weber et al.

[11] Patent Number: 5,728,079
[45] Date of Patent: Mar. 17, 1998

[54] CATHETER WHICH IS VISIBLE UNDER MRI

[75] Inventors: Jan Weber, Roden; Wilhelmus Petrus Martinus Maria van Erp, Leek, both of Netherlands

[73] Assignee: Cordis Corporation, Miami Lakes, Fla.

[21] Appl. No.: 530,682

[22] Filed: Sep. 19, 1995

[30] Foreign Application Priority Data

Sep. 19, 1994 [NL] Netherlands ................ 94.01517
Sep. 19, 1994 [NL] Netherlands ................ 94.01518
Sep. 21, 1994 [NL] Netherlands ................ 94.01533

[51] Int. Cl.$^6$ .................................................. A61M 25/00
[52] U.S. Cl. .................................... 604/280; 128/656
[58] Field of Search .................................. 604/280, 264; 128/653.1, 653.2, 653.4, 654, 656–658, 772; 37/114, 137, 146

[56] References Cited

U.S. PATENT DOCUMENTS

| | | |
|---|---|---|
| 4,827,931 | 5/1989 | Longmore . |
| 4,989,608 | 2/1991 | Ratner .................... 128/653 A |
| 5,154,179 | 10/1992 | Ratner . |
| 5,555,893 | 9/1996 | Hackett et al. .................... 128/772 |

FOREIGN PATENT DOCUMENTS

| | | |
|---|---|---|
| 8504330 | 3/1985 | WIPO . |
| 9401518 | 9/1994 | WIPO . |

*Primary Examiner*—Corrine M. McDermott
*Assistant Examiner*—Cris L. Rodriguez
*Attorney, Agent, or Firm*—Dean L. Garner

[57] ABSTRACT

In accordance with the present invention there is provided a catheter which is visible during magnetic resonance imaging of body tissue. The catheter includes a body having a proximal end, a distal end and at least one lumen extending therethrough. The body is formed from a solid material. The solid material is made from plastic and enough paramagnetic substance to render at least a predetermined portion of the catheter visible during magnetic resonance imaging of body tissue.

6 Claims, 4 Drawing Sheets

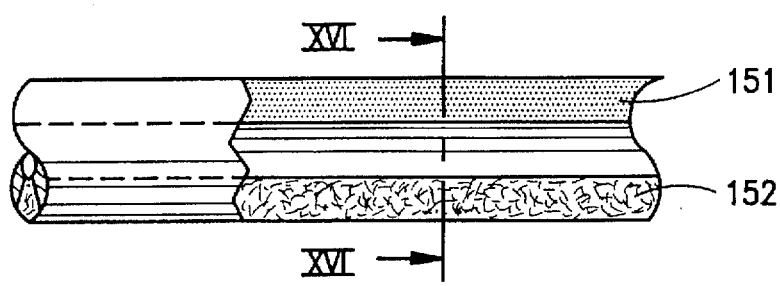 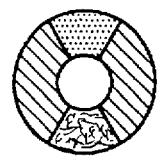
FIG. 15  FIG. 16
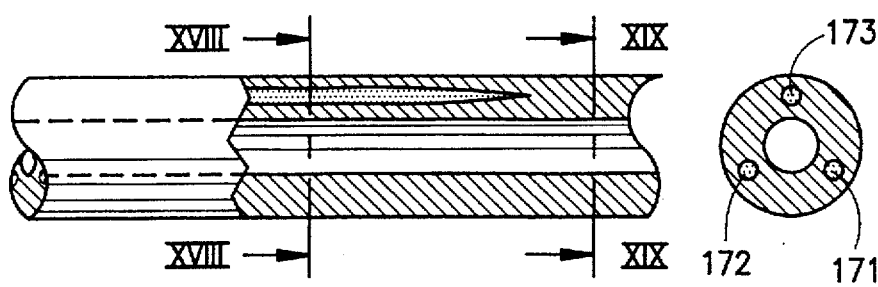 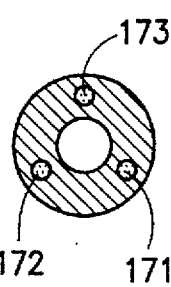
FIG. 17  FIG. 18  FIG. 19
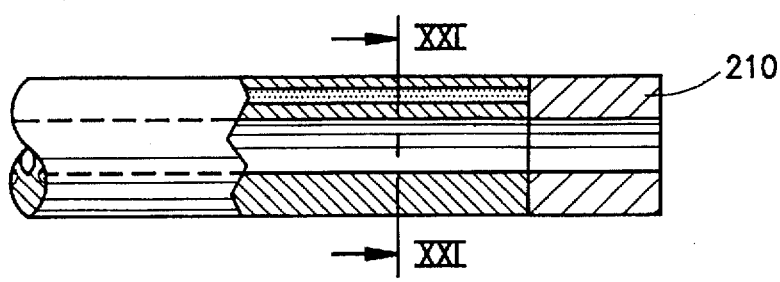 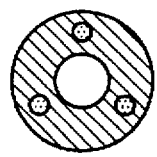
FIG. 20  FIG. 21
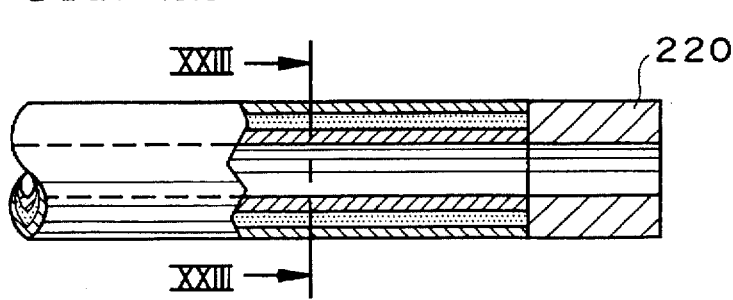 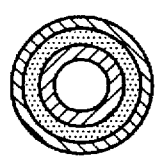
FIG. 22  FIG. 23

CATHETER WHICH IS VISIBLE UNDER MRI

FIELD OF THE INVENTION

The present invention relates to a catheters which are visible under magnetic resonance imaging (MRI) and under X-ray. The present invention has further relation to such catheters which are made from a tube-like body extruded from a plastic material and having a proximal end, a distal end and at least one lumen extending therethrough. The present invention has even further relation to such catheter that are used in medicine for diagnostic and interventional purposes.

BACKGROUND OF THE INVENTION

Catheters are widely used in a number of medical procedures such as percutaneous coronary angioplasty. With certain applications it is standard practice to make the position of the catheter inside the body of the patient visible by means of X-ray imaging. Often the tip of guiding catheters and diagnostic catheters are made from or are coated with radiopaque materials and become clearly visible on an X-ray screen. Examples of such catheters are given in commonly assigned U.S. Pat. Nos. 5,171,232 issued to Castillo et al. on Dec. 15, 1992 and 5,045,072 issued to Castillo et al. on Sep. 3, 1991, both of which are hereby incorporated herein by reference.

However, other medical applications, such as neurology, use procedures which are performed under MRI instead of X-ray. For these applications it is desirable to make catheters visible when employing MRI techniques. An example of such a catheter is shown in U.S. Pat. No. 5,154,179 issued to Ratner on Oct. 13, 1992, which is hereby incorporated herein by reference. That patent discloses a catheter wherein ferromagnetic particles have been incorporated in the material of the body of the catheter. These particles disturb the magnetic field in the MRI device and result in a deviation in the picture which is formed, thus indicating the position of the catheter. However, the ferromagnetic material often causes a severe distortion of the image. The Ratner reference also discloses the use of a liquid paramagnetic material which is injected into a lumen of the catheter to make it visible under MRI. While the image is clearer, many paramagnetic materials are harmful to humans. The use of a liquid paramagnetic material runs the risk that some of it may leak into the patient. Furthermore, the diameter of the catheter must be relatively large to accommodate the limen for the liquid paramagnetic material. This is undesirable, especially for neurological applications. There has, therefore, been a desire to have a catheter which is visible under MRI, has a less distorted picture than that given by using ferromagnetic materials, and which is not harmful to the patient.

SUMMARY OF THE INVENTION

In accordance with the present invention there is provided a catheter which is visible during magnetic resonance imaging of body tissue. The catheter includes a body having a proximal end, a distal end and at least one lumen extending therethrough. The body has a circumference and a longitudinal axis running between the proximal and distal ends. The body is formed from one or more plastics and enough paramagnetic substance to render at least a predetermined portion of the catheter visible during magnetic resonance imaging of body tissue.

BRIEF DESCRIPTION OF THE DRAWINGS

While the specification concludes with claims particularly pointing out and distinctly claiming the subject matter of the invention, it is believed the invention will be better understood from the following detailed description of the invention taken in conjunction with the accompanying drawings in which:

FIG. 15 is a view similar to that of FIG. 1 but showing another alternative embodiment.

FIG. 16 is a cross-sectional view of the catheter of FIG. 15 taken along line XVI—XVI.

FIG. 17 is a view similar to that of FIG. 1 but showing another alternative embodiment.

FIG. 18 is a cross-sectional view of the catheter of FIG. 17 taken along line XVIII—XVIII.

FIG. 19 is a cross-sectional view of the catheter of FIG. 17 taken along line XIX—XIX.

FIG. 20 is a view similar to that of FIG. 1 but showing another alternative embodiment.

FIG. 21 is a cross-sectional view of the catheter of FIG. 20 taken along line XXI—XXI.

FIG. 22 is a view similar to that of FIG. 1 but showing another alternative embodiment.

FIG. 23 is a cross-sectional view of the catheter of FIG. 22 taken along line XXIII—XXIII.

DETAILED DESCRIPTION OF THE INVENTION

Figure 1:
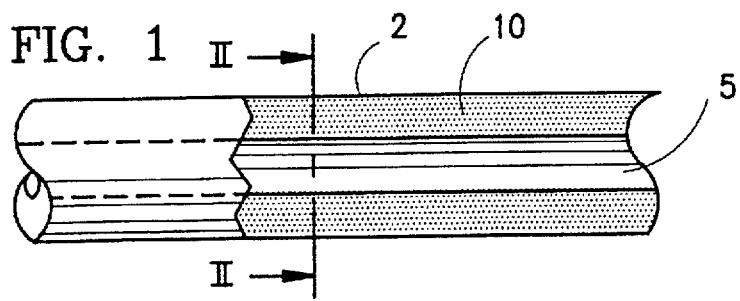
FIG. 1 is a simplified partial cross-sectional view of the catheter of FIG. 24, wherein the section is taken along the longitudinal axis of the catheter.
Figure 2:
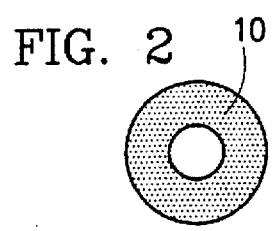
FIG. 2 is a cross-sectional view of the catheter of FIG. 1 taken along line II—II.
Figure 24:
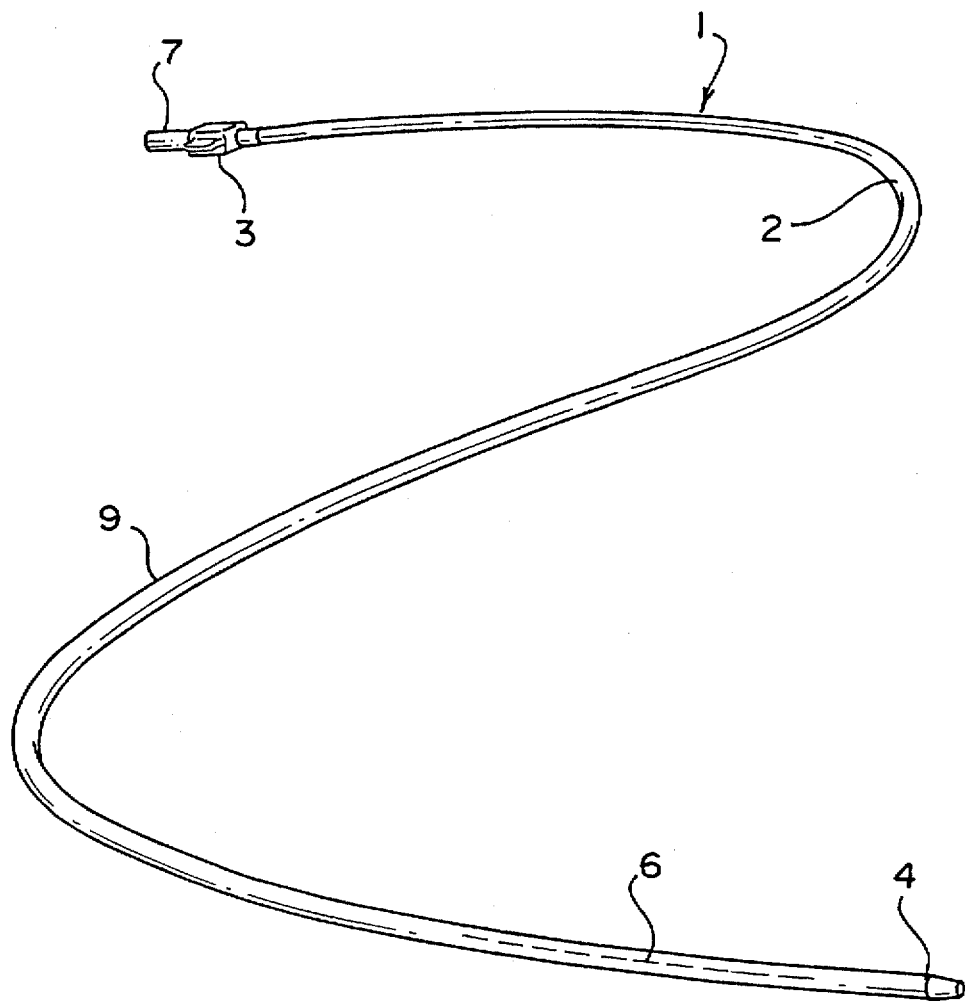
FIG. 24 is a perspective view of the catheter of FIG. 1.

Referring to the drawings in detail wherein like numerals indicate the same element throughout the views there is shown in FIG. 24 a catheter 1 in accordance with the present invention. Catheter 1 includes a body 2 having a proximal end 3 and a hub 7 attached thereto. The body further includes a distal end 4 and at least one lumen 5 (shown in FIG. 1) extending along the longitudinal axis 6 of the catheter 1. As seen from FIGS. 1 and 2, body 2 is made from a paramagnetic compound 10. As used throughout this specification a paramagnetic compound is a solid material comprising a plastic, such as polyurethane, nylon, Teflon or polyethylene, and a paramagnetic substance. The use of a paramagnetic substance gives a clear picture of the catheter under an MRI, but not so distorted, as with ferromagnetic materials. This feature makes the catheter particularly suitable for medical applications done under MRI. The catheters of the present invention are preferably made by extrusion processes which are well known to those of ordinary skill in the art.

Suitable paramagnetic substances include transition metals such as copper, manganese, chromium, nickel and especially gadolinium and dysprosium because of their high susceptibilities. Also mixtures, alloys and salts of these materials have suitable properties for application according to the invention. The quantity of paramagnetic substance is to be used in the plastic material, such as by way of a filler incorporated into the plastic, depends in particular on the properties of the MRI device used for the detection of the catheter. Also the properties of the paramagnetic substance to be used are decisive. With weak paramagnetic substances one will use a stronger concentration of this material than with strong paramagnetic substances. In practice the concentration may vary for instance from 0.001% in the case of strong paramagnetic substances such as dysprosium oxide ($DyO_3$) to 60% in the case of a weak paramagnetic substance such as for instance titanium dioxide. These percentages are percentages by weight.

Figure 3:
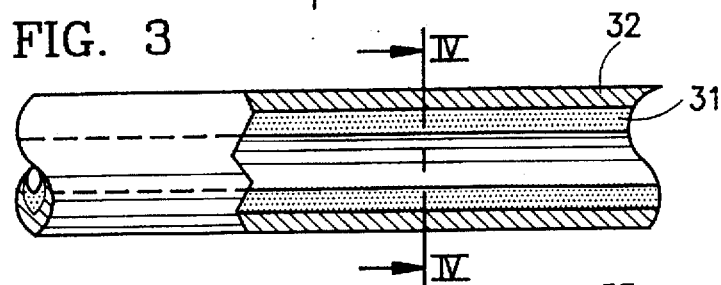
FIG. 3 is a view similar to that of FIG. 1 but showing an alternative embodiment.
Figure 4:
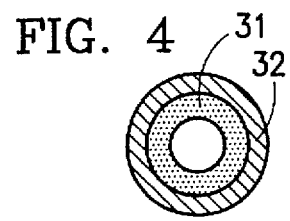
FIG. 4 is a cross-sectional view of the catheter of FIG. 3 taken along line IV—IV.

FIGS. 3 and 4 show an alternative embodiment of the catheter of the present invention wherein the body of the catheter is made up of two concentric layers 31 and 32. The inner layer 31 comprises a paramagnetic compound, whereas the outer layer 32 is free of paramagnetic substance and preferably comprises plastic. Consequently there is no direct contact between body tissue and the inner layer 31 of paramagnetic compound. This is often preferred because many paramagnetic substances are harmful to the human body.

Figure 5:
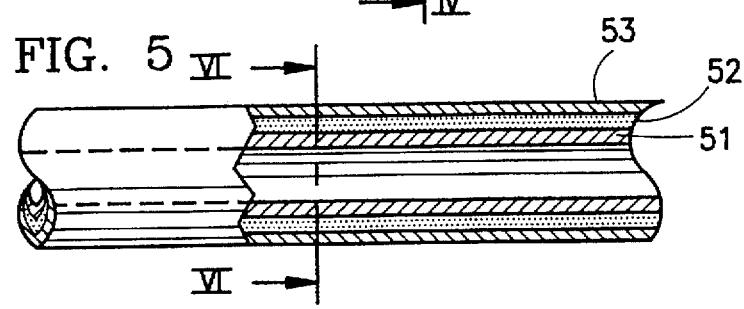
FIG. 5 is a view similar to that of FIG. 1 but showing another alternative embodiment.
Figure 6:
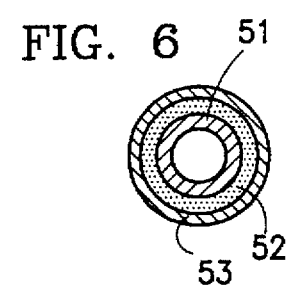
FIG. 6 is a cross-sectional view of the catheter of FIG. 5 taken along line VI—VI.

FIGS. 5 and 6 illustrate an embodiment wherein the catheter has three layers 51, 52 and 53. The intermediate layer 52 comprises paramagnetic compound, whereas the inner layer 51 and outer layer 53 are free of paramagnetic substance and preferably comprise plastic. Because the inner and outer layers are both free of paramagnetic substance, contact of paramagnetic substances with the body is reduced on both the outside and on the inside of the catheter. The lumen of the catheter often conveys fluids which ultimately end up inside the body of the patient. This embodiment reduces the likelihood that such fluids will carry paramagnetic substance from the lumen into the body.

Figure 7:
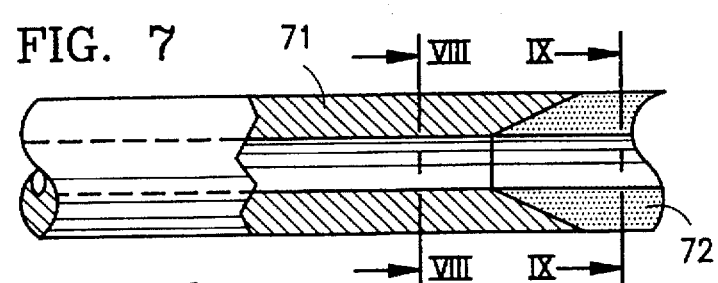
FIG. 7 is a view similar to that of FIG. 1 but showing another alternative embodiment.
Figures 8, 9:
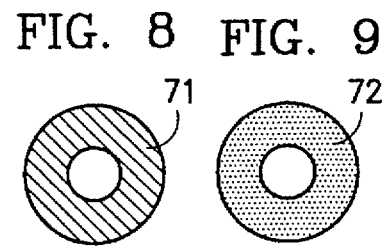
FIG. 8 is a cross-sectional view of the catheter of FIG. 7 taken along line VIII—VIII.
FIG. 9 is a cross-sectional view of the catheter of FIG. 7 taken along line IX—IX.

FIGS. 7, 8 and 9 illustrate an embodiment where only a predetermined length of the catheter body is comprised of a paramagnetic compound. That is the paramagnetic substance does not extend over the entire length of the catheter body. The left-hand section 71 is free of paramagnetic substance and preferably is made from plastic. The right-hand section 72 is made from a paramagnetic compound. The two sections 71 and 72 may have been manufactured separately and bonded together by glueing or the like. This embodiment, where the paramagnetic compound does not extend over the entire length of the catheter, is useful for some medical applications. Sometimes it is only necessary to render part of the catheter, usually the distal end, visible on the MRI screen.

Figure 10:
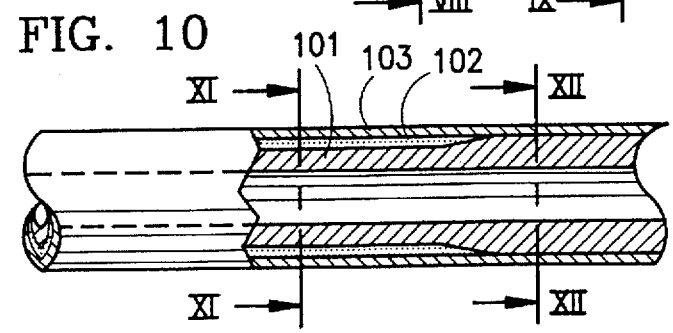
FIG. 10 is a view similar to that of FIG. 1 but showing another alternative embodiment.
Figures 11, 12:
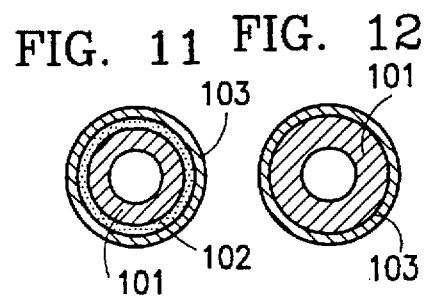
FIG. 11 is a cross-sectional view of the catheter of FIG. 10 taken along line XI—XI.
FIG. 12 is a cross-sectional view of the catheter of FIG. 10 taken along line XII—XII.

The embodiment shown in FIGS. 10, 11 and 12 show a catheter with three layers 101, 102 and 103, similar to the catheter shown in FIGS. 5 and 6. As with the catheter shown in FIG. 7, the intermediate layer 102 is a paramagnetic compound, but it extends only over part of the length of the catheter. FIG. 11 shows a cross section of that part of the catheter which comprises three layers, whereas FIG. 12 shows a cross-section along line XII—XII where the catheter only has the two layers 101 and 103 made from plastic. The layers may have been formed simultaneously by co-extrusion or any other type of extrusion. This embodiment can be manufactured by cutting off the supply of the paramagnetic compound, during the extrusion process. This embodiment is preferred in that the paramagnetic compound cannot come into contact with the surrounding tissue.

Figure 13:
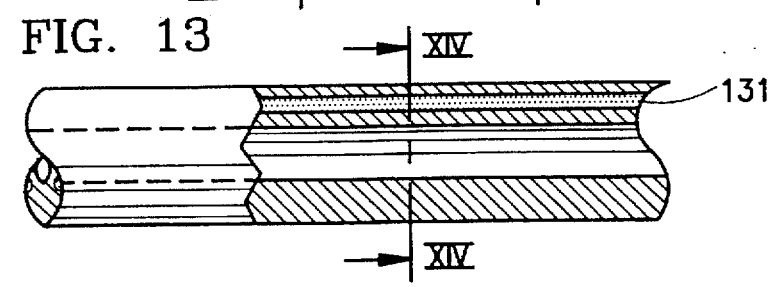
FIG. 13 is a view similar to that of FIG. 1 but showing another alternative embodiment.
Figure 14:
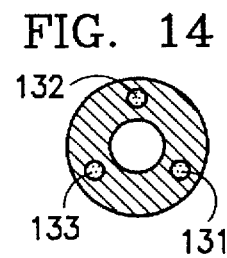
FIG. 14 is a cross-sectional view of the catheter of FIG. 13 taken along line XIV—XIV.

The embodiments shown in FIGS. 13 and 14, show a catheter wherein the paramagnetic compound is disposed within the catheter as three strips 131, 132 and 133. Preferably, the strips are completely surrounded by plastic, so that the compound 10 has no contact with the surrounding tissue.

FIGS. 15 and 16 illustrate an embodiment of a catheter in accordance with the present invention wherein the body is made from two strips 151 and 152 of different materials. Strip 151 is made from paramagnetic compound. Strip 152 is made from a compound of plastic and a radiopaque substance such as bismuth salts or the like. This embodiment is, therefore, clearly visible both on an MRI screen and on an X-ray screen. The paramagnetic compound and the radiopaque substance could be mixed together and disposed on one strip the strip could rotate axially to obtain better mechanical features.

FIGS. 17, 18 and 19 show an embodiment similar to that shown in FIG. 13, wherein the strips 171, 172 and 173 of paramagnetic compound are reduced from the proximal end of the catheter towards the distal end of the catheter and eventually tapering off completely.

FIGS. 20 and 21 show an embodiment of a catheter similar to that shown in FIG. 17. However, instead of tapering the paramagnetic substance down from the proximal to distal ends, the distal tip 210 is made completely from a non-paramagnetic substance which is connected to the catheter. Preferably distal tip 210 is made of a softer plastic material than the plastic used proximal thereto so it is as less traumatic as possible.

A similar solution is obviously possible with a catheter of the embodiment as shown in FIG. 5. In FIG. 22 the distal tip 220 is made completely from a non-paramagnetic substance which is connected to the catheter.

Figure 25:
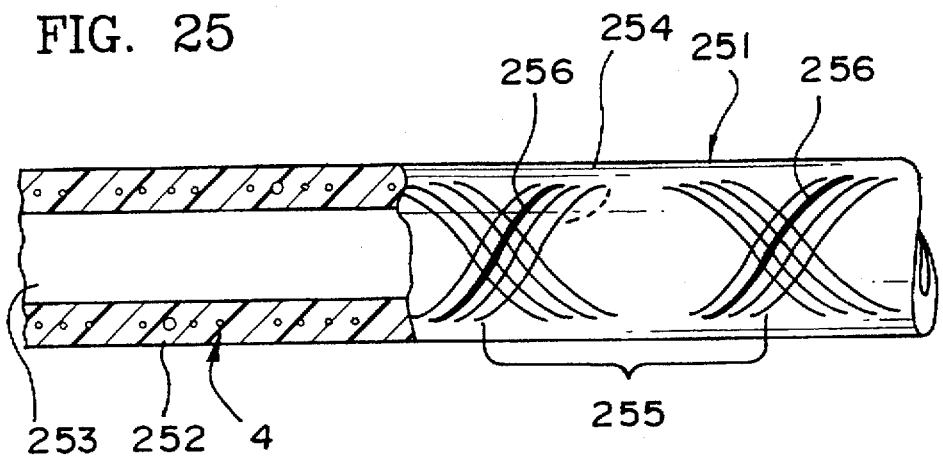
FIG. 25 is a view similar to that of FIG. 1 but showing another alternative embodiment.

Often catheters of the type described herein are made from plastic and have at least one reinforcing layer comprising braided wires. Catheters of this type are described in U.S. Pat. Nos. 3,485,234 issued to Stevens on Dec. 23, 1969 and 3,585,707 issued to Stevens on Jun. 22, 1971, both of which are hereby incorporated herein by reference. The embodiment of the catheter of the present invention disclosed in FIG. 25, shows a catheter 251 having a tube-like body 252 with a lumen 253. Body 252 comprises a plastic having a reinforcing layer 254 comprising a braided of metal wire. Layer 254 comprises two different types of metal wire. Wires 256 are made from a paramagnetic substance, wherein wires 255 have been made of a non-magnetic material. Wires 255 remain invisible under MRI conditions, whereas wires 256 cause just enough disturbance of the uniformity of the magnetic field, to render the catheter visible on the screen. Wires 256 are preferably made from an alloy of non-magnetic material and a strong paramagnetic substance, such as an alloy of titanium and copper or nickel.

Figure 26:
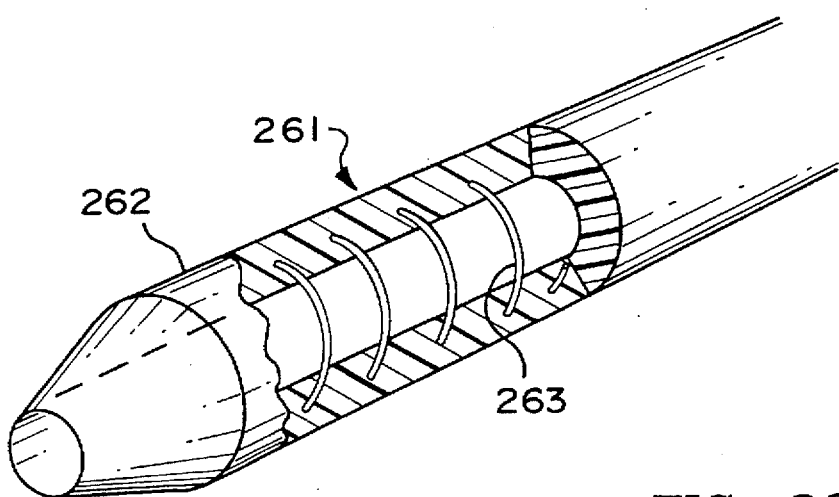
FIG. 26 is a perspective view of another alternative embodiment of a catheter of the present invention, having a cut out section similar to that of FIG. 1.

Another embodiment of the present invention is disclosed in FIG. 26 where there is shown catheter 261. Catheter 261 has a helically wound wire 263 embedded in the plastic material of the body 262. Wire 263 is screened off by plastic material which the body 262 has been made, so that there is not objection to choose paramagnetic substances for the wire 263, material which has optimal properties where image formation under MRI conditions is concerned but which as such may be harmful to humans. By winding the wire in a helical fashion, it does not effect the flexibility of the distal end of the catheter 261.

While particular embodiments of the present invention have been illustrated and described herein, various modifications will be apparent to those skilled in the art without departing from the spirit and scope of the present invention. Accordingly, the scope of the present invention should be considered in terms of the following claims and is understood not to be limited to the details described and shown in the specification and drawings.

That which is claimed is:

1. A catheter which is visible during magnetic resonance imaging of body tissue, said catheter comprising:

a body having a proximal end, a distal end and at least one lumen extending therethrough, said body having a circumference and a longitudinal axis running between said distal and proximal ends, said body having a number of coaxial layers wherein at least one layer is formed of plastic and at least one layer comprises enough solid paramagnetic substance to render at least a predetermined portion of said catheter visible during magnetic resonance imaging of body tissue.

2. A catheter according to claim 1, wherein one of said coaxial layers comprises a braided wire reinforcing layer wherein a predetermined portion of said braided wire comprises a paramagnetic substance.

3. A catheter according to claim 2 wherein said braided wire comprising paramagnetic material comprises an alloy of non-magnetic material and a strong paramagnetic material.

4. A catheter according to claim 3, wherein the alloy comprises at least one material from the group including titanium, copper and nickel.

5. The catheter according to claim 1 wherein the coaxial layer comprising paramagnetic substance is sandwiched between two layers of plastic material being substantially free from paramagnetic substance.

6. A catheter according to claim 1 wherein the paramagnetic substance has been chosen from the group comprising: copper, manganese, chromium, nickel, gadolinium, dysprosium and mixtures, alloys and salts thereof.

\* \* \* \* \*